United States Patent [19]

Mayr et al.

[11] 4,092,422

[45] May 30, 1978

[54] SYNERGISTIC FUNGICIDAL MIXTURE OF CAPTAFOL AND THIABENDAZOL

[75] Inventors: Alois Mayr, Munich; Max Königer, Rothschwaige; Gustav Obermayer, Munich, all of Germany

[73] Assignee: Consortium fur Elektrochemische Industrie GmbH, Munich, Germany

[21] Appl. No.: 670,815

[22] Filed: Mar. 26, 1976

[30] Foreign Application Priority Data

Apr. 3, 1975 Germany ............................ 2514460

[51] Int. Cl.² .................. A01N 9/12; A01N 9/22; A01N 9/02
[52] U.S. Cl. ...................................... 424/270; 424/274
[58] Field of Search ............................... 424/270, 274

[56] References Cited

U.S. PATENT DOCUMENTS 3,178,447   4/1965   Kohn ................................. 424/248

OTHER PUBLICATIONS

Chemical Week, Jul. 26, 1972, "Pesticides' 72".

*Primary Examiner*—V. D. Turner
*Attorney, Agent, or Firm*—Allison C. Collard

[57] ABSTRACT

A fungicide mixture for combatting stem-breaking diseases and spike or ear diseases in cereals and corn, comprising from 50 to 90 percent by weight of N-(1,1,2,2-tetrachloroethylthio)-3a,4,7,7a-tetrahydrophthalimide and from 50 to 10 percent by weight of 2-(4'-thiazolyl)-benzimidazole, based on the total weight of the two components.

3 Claims, No Drawings

SYNERGISTIC FUNGICIDAL MIXTURE OF CAPTAFOL AND THIABENDAZOL

The present invention relates to fungicides suitable for application to cereals and to corn so as to protect them against stem and spike or ear diseases.

The cultivation of cereals and corn is suffering increasingly from the mentioned diseases. This is partly because new high-production types of cereal or corn do not have an adequate resistance to or tolerance of these diseases, but it is mainly attributable to the use of very limited crop rotations or even monoculture. The continual cultivation of a single type of crop on the same ground gives the respective parasites the best opportunity of developing, whereas where crops are rotated, the parasites are deprived of their source of life for a considerable period.

The fungicides presently used often give only inadequate protection of the cereal cultures against stem and spike or ear diseases, with the result that there are crop losses as a result of stem breakage and spike or ear diseases.

A frequently used fungicide known under the trade name "Captafol" is N-(1,1,2,2-tetrachloroethylthio)-3a,4,7,7a-tetrahydrophthalimide. It is effective against cercosporella and septoria if applied at the right time. On the other hand, if applied after infection, it is of little effect. In practice, the optimum application time depends on the weather and the time of infection and cannot readily be predetermined by the farmer. For this reason, the fungicide is often applied twice, in order to increase the chances of success. Mildew, stem fusaria and spike or ear fusaria, cannot be combatted with captafol in any case.

It is the object of the present invention to provide means which are effective against all the above-named diseases and which can be applied at any desired time without the above-mentioned limitations.

It has been found according to the invention that a combination of comprising from 50 to 90 percent by weight of N-(1,1,2,2-tetrachloroethylthio)-3a,4,7,7a-tetrahydrophthalimide and from 50 to 10 percent by weight of 2-(4'thiazolyl)-benzimidazole, based on the total weight of the two components, is an eminently effective fungicide against the mentioned diseases. 2-(4'thiazolyl)-benzimidazole (commercially available as "Thiabendazol" is known as a fungicide but has not been used at all in cereal cultivation since it is of little effect).

The present invention also provides a fungicide preparation comprising, as active substances, N-(1,1,2,2-tetrachloroethylthio)-3a,4,7,7a-tetrahydrophthalimide and 2-(4' thiazolyl)-benzimidazole in a respective weight ratio of from 50 : 50 to 90 : 10, in admixture or conjunction with a diluent.

It has surprisingly been found that the mixture according to the invention is effective in combatting the stem-breaking diseases cercosporella and stem fusaria, as well as the spike or ear diseases septoria, mildew and ear fusaria. This is particularly surprising because, as mentioned above, 2-(4' thiazolyl)-benzimidazole (Thiabendazol) alone has little effect in cereal cultivation. Moreover, the present mixture allows a much larger margin in the application time, in contrast to captafol which permits little margin. The present mixture allows a margin of six to eight weeks in combatting stem breakage and a margin of up to four weeks in combatting spike or ear diseases. These margins are, of course, relative to the time at which the respective diseases normally occur. That is to say, in the case of spike or ear diseases in cereal development stages (according to Feekes scale) M to R, preferably N to P, and in the case of stem diseases in stages E to L, preferably F to J. It is thus unnecessary to apply the fungicide more than once in order to ensure that it will be effective, in contrast to "captafol" used alone.

A further advantage of the present mixture is that the total amount of active substances applied may be less than that previously required while still giving an improved effect as manifested by better crop yields. Moreover, it was surprisingly found that diseases which were very hard to combat up to now, such as *ophiobulus graminis,* were simultaneously counteracted by the fungicide combination according to the invention.

The fungicide mixture of the invention is particularly suitable for use in the cultivation of cereals, and especially summer and winter barley, summar and winter wheat, and rye as well as corn. It can also be used to advantage in the cultivation of rice, in the case of a fusarium attack, for example. The necessary amounts calculated per hectare range from 500 g to 5 kg, preferably 700 g to 3 kg of the effective mixture, preferably 60 to 80 percent by weight of Captafol and 20 to 40 percent by weight of Thiabendazol.

The fungicide mixture per se can be applied to the crops. It is more usual, however, for the mixture to be formulated in known manner into fungicidal preparations more suitable for sale and transport and/or for application, such as emulsion concentrates, pastes, spraying and dusting agents. Such preparations advantageously contain from 0.1 to 95 percent by weight of the active substances, based on the total weight of the preparation. The pastes, emulsion concentrates and spraying powders are usually further diluted with water prior to use so as to form spraying liquors more suitable for application to the crops. These advantageously contain from 0.0001 to 5 percent by weight, preferably from 0.05 to 2.5 percent by weight, of the active substances based on the total weight of the preparation.

If necessary, the fungicidal mixtures can be applied together with other chemicals used in agriculture, e.g., fertilizers or herbicides. A preparation in the form of an emulsion concentrate advantageously comprises from 10 to 60 percent by weight of the active substances, from 2 to 25 percent by weight of a dispersant, based on the total weight of the preparation, and an organic solvent. Suitable dispersants are, for example, sodium alkylbenzene sulphonates, calcium dodecylbenzene sulphonate, alkyl polyglycol ethers, alkylphenol ethylene oxide condensation products and sodium alkylnaphthalene sulphonates. Suitable organic solvents are, for example, aromatic hydrocarbons, e.g., benzene, toluene, xylene, and aromatic naphtha and/or aliphatic and cycloaliphatic liquids, for example, ketones, e.g., acetone and cyclohexanone, alcohols, e.g., ethanol and isopropanol, and ethers.

A spraying powder advantageously contains from 10 to 80 percent by weight of the active substances, from 20 to 80 percent by weight of an inert filler, and a few percent by weight of a dispersant. Suitable fillers are, for example, kaolin, montmorillonite, china clay, magnesium carbonate, calcium carbonate, kieselguhr, highly dispersed silica, fuller's earth, talc and pyrophyllite. Examples of suitable dispersants are those given above.

Suitable dusts are those containing from 5 to 25 percent by weight of the active substances and an inert filler, for example, those mentioned above.

The pulverulent fungicidal preparations are suitably manufactured by intimately mixing the various components and grinding the mixture in a bouncing pin mill or other suitable grinding device to a grain size of less than 20 μ, again mixing the components, and finally sieving the mixture.

The present invention also provides a method of combatting fungi on crops, which comprises applying to the crops or to a crop area a fungicide mixture according to the invention or a fungicidal preparation according to the invention.

The mixture or preparation is advantageously applied in such an amount that the quantity of the active substances applied is from 500 g/ha to 5/kg/ha, preferably from 700 g/ha to 3 kg/ha.

The following examples illustrate the present invention by giving the results of applying to various infected cereals and to corn a fungicidal preparation of the invention in comparison to a conventional fungicidal preparation.

A. Preparations

The two preparations used were as follows:
(1) fungicidal preparation according to the invention contained in 1000 g - 220 g Thiabendazol.
    600 g Captafol.
    180 g auxiliaries.
(2) Comparison fungicidal preparation contained in 1000 g - 800 g Captafol.
    200 g auxiliaries.

There were made up into spraying liquors of various concentrations such that the required amounts of the active substances, as specified below, could be applied to the crops.

B. Application

These preparations were applied to infected crops in the cereal development stages indicated in the examples in E and H against stem-breaking disease and in N/O against ear or spike diseases.

The preparations were applied to the crops using an allotment knapsack sprayer having a working width of 2.5 m. In the case of each test, application was made to four plots, each 10 m × 2.5 m. Application was made using a spraying pressure of 3.5 atmospheres gage and a coverage of 400 l/ha.

After ripening of the cereal, a central strip 10 m × 1.75 m was harvested from each plot using a plot combineharvester.

C. Evaluation

The yield and the 1000-grain weight (TGW) were calculated for each test and in the tables below are expressed in percentages with respect to a control test in which the crops were not treated (taken as 100 percent).

The average percentage infection values (IV) are given in the tables below and were calculated as follows:
(a) Stem breaking diseases Calculation was effected according to the guidelines laid down by the German Federal Biological Institute (*Biologische Bundesanstalt*):
% IV = ½ (% slightly disposed stems) + (% severely diseases stems).

(b) Spike or ear diseases
Infection was divided into five classes numbered 1 to 5 as follows:
1 = no infection
2 = up to 10% infection
3 = 10 to 25% infection
4 = 25 to 50% infection
5 = 50 to 100% infection The number of spikes or ears in each infection class were determined and are given by $N_1$, $N_2$, $N_3$, $N_4$ and $N_5$ respectively. The total number of spikes or ears examined is given by N. The average infection value was then calculated as follows:

$$\% IV = \frac{(O\,N_1 + 10\,N_2 + 25\,N_3 + 50\,N_4 + 100\,N_5)}{N}$$

The tables below also indicate the amount of the active substances applied (kg/ha) and the cereal development stage (Feekes scale) at which application was made, in the case of each test.

EXAMPLE 1

Combatting Stem-Breaking Diseases in Winter Wheat

Winter wheat was sprayed as described under B above and evaluated, 77 days after application (or after the second application, when two were made), for the occurrence of the stem diseases cercosporella and fusarium. The results are given in Table 1.

Table 1

| Application Amount kg/ha | Stage | Comparison Fungicide IV | Yield | TGW | Fungicide of Invention IV | Yield | TGW |
|---|---|---|---|---|---|---|---|
| 2.0 | E | 65 | 105.6 | 102.9 | 52 | 111.5 | 104.7 |
| 2.0 | F | 57 | 108.2 | 105.0 | 50 | 112.0 | 104.2 |
| 1.0 | G | 62 | 103.6 | 108.6 | 48 | 110.5 | 106.9 |
| 2.0 | G | 57 | 104.0 | 101.0 | 35 | 114.3 | 109.9 |
| 2.0 | H | 44 | 101.0 | 101.7 | 41 | 114.8 | 107.9 |
| 2×2 | F+H | 47 | 109.4 | 102.5 | | | |
| 2×1 | F+H | 60 | 109.0 | 103.2 | | | |
| Untreated | | 76 | 100.0 | 100.0 | | | |

EXAMPLE 2

Combatting Stem Breaking Diseases In Summer Wheat

Summer wheat was sprayed, and evaluated, 37 days after application, for the occurrence of the stem diseases cercosporella, fusarium and rhizoctonia, which occurred in the approximate ratio 6 : 3 : 1 respectively. The tests were carried out in the manner described in B. The results are given in Table 2.

Table 2

| Application Amount kg/ha | Stage | Comparison Fungicide IV | Yield | TGW | Fungicide of Invention IV | Yield | TGW |
|---|---|---|---|---|---|---|---|
| 2.0 | F | 20.8 | 114 | 106 | 9.7 | 120 | 113 |
| 1.0 | F | 28.1 | 102 | 105 | 22.5 | 111 | 108 |
| 2.0 | G | 27.3 | 110 | 108 | 14.7 | 118 | 109 |
| 2.0 | H | 32.9 | 107 | 108 | 13.7 | 116 | 117 |
| Untreated | | 63.3 | 100 | 100 | | | |

EXAMPLE 3

Combatting Spike Diseases In Winter Wheat

Winter wheat was sprayed in stage N/O as described in B, and evaluated 35 days later for the occurrence of spike diseases as explained in C. The results are given in Table 3.

Table 3

| Application | | Comparison Fungicide | | | Fungicide of Invention | | |
|---|---|---|---|---|---|---|---|
| Amount kg/ha | Stage | IV | Yield | TGW | IV | Yield | TGW |
| 1.5 | N/O | | | | 12 | 118.8 | 123.7 |
| 2.0 | N/O | 21 | 114.6 | 118.0 | 12 | 125.1 | 129.3 |
| 2.5 | N/O | 16 | 118.7 | 122.3 | | | |
| 3.0 | N/O | 15 | 116.5 | 120.6 | | | |
| Untreated | | 56 | 100.0 | 100.0 | | | |

EXAMPLE 4

Combatting Spike Diseases In Summer Wheat

Summer wheat was sprayed in stage N/O as described in B, and evaluated after 35 days for the occurrence of spike diseases. The results are given in Table 4.

Table 4

| Application | | Comparison Fungicide | | | Fungicide of Invention | | |
|---|---|---|---|---|---|---|---|
| Amount kg/ha | Stage | IV | Yield | TGW | IV | Yield | TGW |
| 1.5 | N/O | | | | 47 | 127.2 | 127.9 |
| 2.0 | N/O | 48 | 124.0 | 120.4 | 38 | 130.9 | 128.3 |
| 2.5 | N/O | 41 | 128.3 | 124.7 | | | |
| 3.0 | N/O | 44 | 128.6 | 124.2 | | | |
| Untreated | | 85 | 100.0 | 100.0 | | | |

EXAMPLE 5

Winter wheat was sprayed in stages N, Q and R, and evaluated as in Example 3. The results are given in Table 5.

Table 5

| Application | | Comparison Fungicide | | | Fungicide of Invention | | |
|---|---|---|---|---|---|---|---|
| Amount kg/ha | Stage | IV | Yield | TGW | IV | Yield | TGW |
| 2.0 | N | 25.7 | 114.6 | 116.6 | 14.5 | 125.1 | 123.4 |
| 2.0 | Q | 32.0 | 113.4 | 116.5 | 22.4 | 124.3 | 122.1 |
| 2.0 | R | 60.5 | 105.7 | 106.6 | 32.8 | 117.2 | 116.2 |
| Untreated | | 68.8 | 100.0 | 100.0 | | | |

EXAMPLE 6

Combatting Ophiobolus Graminis In Summer Wheat

The application of the agent is carried out as per B in the stages F, G, and H of the Feekes Scale, evaluation according to C occurred 60–70 days after application.

In Table 6, the IV are given for "untreated" for Thiabendazol and Captafol, single components, and for the combination according to the invention. The surprising effect of the combination is apparent.

Table 6

| Application | Stage | Amount g/Ha | IV Ophiobolus Graminis |
|---|---|---|---|
| Untreated | — | — | 17.3 |
| Inventive Combination | F | 1500 | 4.6 |
| " | G | 1500 | 6.5 |
| " | H | 1500 | 2.4 |
| Thiabendazol 60% | G | 750 | 22.9 |
| | H | 750 | 26.3 |
| Captafol 80% | F | 2000 | 14.3 |
| | G | 2000 | 18.8 |
| | H | 2000 | 21.7 |

EXAMPLE 7

Combatting Stem Disease Of Corn

| | |
|---|---|
| Plot size | 50 m² |
| Distance of Rows | 60 cm |
| Distance of Plants in one Row | 17 cm |
| Each plot has 3 rows of | 30 m length |
| Number of Repeats | 4 |
| Brand of Corn | Inracorn |
| Amount of Water | 600 l/ha |
| Spraying Device | Knapsack Sprayer, holder with 1.5 m width spraying bars |
| Spraying Pressure | 3.5 atm. gage |
| Nozzle type | Teejet 2-60-6501 |

Evaluation

For determining the infection values, only the center row of each plot, consecutively 100 plants were evaluated. For each test number, four plots were evaluated and a mean value was calculated therefrom. In corn, stem breakage is the main criterium for the effectiveness of the fungicide.

| | Calculation of the IV |
|---|---|
| Classes of Infection | 1 = No infection. |
| | 2 = Slight infection (distinctive damage signs, but not complete breakage of plant stem. |
| | 3 = Strong infection, plant broken. |

$$\% \text{ IV} = \frac{\text{Percentage of slightly broken stems}}{2} + \text{percentage of highly infected stems}$$

Test I

| | Spraying Occurred on July 14 | | |
|---|---|---|---|
| Test Sample No. | Preparation | Amount kg/ha | % IV |
| 1 | Control | Untreated | 54 |
| 2 | Inventive Combination | 2 kg | 19 |

Test II

| | Spraying Occurred On July 29 | | |
|---|---|---|---|
| Test Sample No. | Preparation | Amount kg/ha | % IV |
| 1 | Control | Untreated | 54 |
| 2 | Inventive Combination | 2 kg | 17 |

Test III

| | Spraying Occurred on August 11 | | |
|---|---|---|---|
| Test Sample No. | Preparation | Amount kg/ha | % IV |
| 1 | Control | Untreated | 54 |
| 2 | Inventive Combination | 2 kg | 21 |

Evaluation of the tests were made on September 20.

From the foregoing description, one skilled in the art can easily ascertain the essential characteristic of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A method for combatting stem diseases and spike or ear diseases in crops of cereals and corn, which comprises applying to said crops a synergistic fungicide mixture containing as active substances from 50 to 90% by weight of N-(1,1,2,2-tetrachloroethylthio)-3a,4,7,7a-tetrahydrophthalimide and from 50 to 10% by weight of 2-(4'-thiazolyl)-benzimidazole, in conjunction with a diluant.

2. The method according to claim 1, wherein the fungicide mixture is in the form of a spraying liquor containing from 0.05 to 2.5% by weight of the active substances based on the total weight of the spraying liquor.

3. The method according to claim 1, wherein the total amount of the active substances applied to an area is from 700 g/ha to 3kg/ha.

* * * * *

UNITED STATES PATENT OFFICE
CERTIFICATE OF CORRECTION

Patent No. 4,092,422　　　　　　　　　　Dated　May 30, 1978

Inventor(s)　ALOIS MAYR ET AL

It is certified that error appears in the above-identified patent and that said Letters Patent are hereby corrected as shown below:

Column 2, line 5, delete "Feekes scale" and substitute therefor--the scale of the German Federal Biological Institute referred to as the BBA scale--. Column 4, line 20, delete "Feekes" and substitute therefor--BBA--. Column 5, line 49, delete "Feekes" and substitute therefor--BBA--.

Signed and Sealed this

Twentieth Day of February 1979

[SEAL]

Attest:

RUTH C. MASON
Attesting Officer

DONALD W. BANNER
Commissioner of Patents and Trademarks